(12) United States Patent
Terrill (10) Patent No.: US 7,220,283 B2
(45) Date of Patent: May 22, 2007

(54) PROSTHESIS INCLUDING A MECHANISM FOR ATTACHING A FIRST COMPONENT TO A SECOND COMPONENT

(75) Inventor: Lance Nathan Terrill, Gainesville, FL (US)

(73) Assignee: Exactech, Inc., Gainesville, FL (US)

( * ) Notice: Subject to any disclaimer, the term of this patent is extended or adjusted under 35 U.S.C. 154(b) by 47 days.

(21) Appl. No.: 11/042,367

(22) Filed: Jan. 24, 2005

(65) Prior Publication Data
US 2006/0167557 A1 Jul. 27, 2006

(51) Int. Cl.
*A61F 2/32* (2006.01)
(52) U.S. Cl. .................................................. 623/22.44
(58) Field of Classification Search ............. 623/19.12, 623/20.15, 22.27, 22.28, 22.29, 22.42, 22.43, 623/22.44, 22.45, 22.46, 23.12, 23.13, 23.14
See application file for complete search history.

(56) References Cited

U.S. PATENT DOCUMENTS

| | | | |
|---|---|---|---|
| 1,817,808 A | | 8/1931 | Eaton |
| 2,367,213 A | | 1/1945 | Harding |
| 3,258,284 A | | 6/1966 | Phipps |
| 3,707,107 A | | 12/1972 | Bieri |
| 3,987,499 A | | 10/1976 | Scharbach et al. |
| 4,012,795 A | * | 3/1977 | Dorre et al. ............. 623/22.46 |
| 4,040,756 A | | 8/1977 | Donegan |
| 4,058,856 A | * | 11/1977 | Doerre et al. ............. 623/23.42 |
| 4,225,981 A | | 10/1980 | Zeibig |
| 4,528,702 A | * | 7/1985 | Frey ......................... 623/23.12 |
| 4,921,500 A | | 5/1990 | Averill et al. |
| 5,015,257 A | | 5/1991 | Crowninshield et al. |
| 5,362,311 A | * | 11/1994 | Amino et al. ............. 623/22.45 |
| 5,584,629 A | | 12/1996 | Bailey et al. |
| 5,865,850 A | | 2/1999 | Matthews |
| 6,096,084 A | | 8/2000 | Townley |
| 6,336,941 B1 | * | 1/2002 | Subba Rao et al. ...... 623/22.42 |
| 6,451,057 B1 | * | 9/2002 | Chen et al. ............. 623/17.15 |
| 6,591,475 B2 | | 7/2003 | Ninomiya et al. |
| 6,607,560 B1 | | 8/2003 | Pfaff et al. |
| 6,609,288 B2 | | 8/2003 | Ninomiya et al. |
| 6,840,770 B2 | * | 1/2005 | McDevitt ..................... 433/173 |
| 6,863,530 B2 | * | 3/2005 | McDevitt ..................... 433/173 |
| 2002/0031675 A1 | | 3/2002 | Coles et al. |
| 2004/0015238 A1 | * | 1/2004 | Buehler et al. .......... 623/22.12 |
| 2004/0063069 A1 | * | 4/2004 | Lombardi ..................... 433/173 |

OTHER PUBLICATIONS

Richter, Willmann, Wimmer and Osthues, "Influence of the Ball/Stem-Interface on the Load Bearing Capability of Modular Total Hip Endoprostheses," Modularity of Orthopedic Implants, ASTM STP 1301, Marlowe and Mayor, Eds., American Society for Testing and Materials, 1997.

\* cited by examiner

*Primary Examiner*—Corrine McDermott
*Assistant Examiner*—Thomas J. Sweet
(74) *Attorney, Agent, or Firm*—Greenberg Traurig, LLP (57) ABSTRACT

In one embodiment of the present invention a prosthesis including a mechanism for attaching a first component to a second component is provided. In one example (which example is intended to be illustrative and not restrictive), the first component may be a femoral head component and the second component may be a femoral stem component. In another example (which example is intended to be illustrative and not restrictive), the femoral head component may comprise a ceramic material and the femoral stem component may comprise a metallic material (e.g., any desired orthopedic alloy, such as Cobalt Chromium).

22 Claims, 6 Drawing Sheets

| | A | B | C | D | E | F | G | H | I | J |
|---|---|---|---|---|---|---|---|---|---|---|
| 1 | | | | | | | | | | |
| 2 | | | | | | | | | | |
| 3 | | | | | RADIUS | | | | | |
| 4 | | | | | THREAD DEPTH VALUES | | | | | |
| 5 | | | 0.002 | 0.004 | 0.006 | 0.008 | 0.010 | 0.012 | 0.014 | 0.015 |
| 6 | PITCH | | | | | | | | | |
| 7 | | 0.002 | 2.679E-04 | 1.270E-04 | 8.392E-05 | 6.275E-05 | 5.013E-05 | 4.174E-05 | 3.576E-05 | 3.337E-05 |
| 8 | | 0.003 | 6.771E-04 | 2.919E-04 | 1.905E-04 | 1.419E-04 | 1.131E-04 | 9.412E-05 | 8.059E-05 | 7.519E-05 |
| 9 | | 0.004 | 2.000E-03 | 5.359E-04 | 3.431E-04 | 2.540E-04 | 2.020E-04 | 1.678E-04 | 1.436E-04 | 1.339E-04 |
| 10 | | 0.005 | #NUM! | 8.775E-04 | 5.456E-04 | 4.007E-04 | 3.175E-04 | 2.633E-04 | 2.250E-04 | 2.098E-04 |
| 11 | | 0.006 | #NUM! | 1.354E-03 | 8.038E-04 | 5.838E-04 | 4.606E-04 | 3.810E-04 | 3.252E-04 | 3.031E-04 |
| 12 | | 0.007 | #NUM! | 2.064E-03 | 1.127E-03 | 8.063E-04 | 6.325E-04 | 5.218E-04 | 4.446E-04 | 4.140E-04 |
| 13 | | 0.008 | #NUM! | 4.000E-03 | 1.528E-03 | 1.072E-03 | 8.348E-04 | 6.863E-04 | 5.836E-04 | 5.432E-04 |
| 14 | | 0.009 | #NUM! | #NUM! | 2.031E-03 | 1.386E-03 | 1.070E-03 | 8.757E-04 | 7.429E-04 | 6.909E-04 |
| 15 | | 0.010 | #NUM! | #NUM! | 2.683E-03 | 1.755E-03 | 1.340E-03 | 1.091E-03 | 9.233E-04 | 8.579E-04 |
| 16 | | 0.011 | #NUM! | #NUM! | 3.602E-03 | 2.191E-03 | 1.648E-03 | 1.335E-03 | 1.126E-03 | 1.045E-03 |
| 17 | | 0.012 | #NUM! | #NUM! | 6.000E-03 | 2.708E-03 | 2.000E-03 | 1.608E-03 | 1.351E-03 | 1.252E-03 |
| 18 | | 0.013 | #NUM! | #NUM! | #NUM! | 3.336E-03 | 2.401E-03 | 1.913E-03 | 1.600E-03 | 1.481E-03 |
| 19 | | 0.014 | #NUM! | #NUM! | #NUM! | 4.127E-03 | 2.859E-03 | 2.253E-03 | 1.876E-03 | 1.734E-03 |
| 20 | | 0.015 | #NUM! | #NUM! | #NUM! | 5.216E-03 | 3.386E-03 | 2.633E-03 | 2.178E-03 | 2.010E-03 |
| 21 | | 0.016 | #NUM! | #NUM! | #NUM! | 8.000E-03 | 4.000E-03 | 3.056E-03 | 2.511E-03 | 2.311E-03 |
| 22 | | | | | | | | | | |
| 23 | | | | | | | | | | |

FIG.5A

| | A | B | K | L | M | N | O | P | Q | R | S |
|---|---|---|---|---|---|---|---|---|---|---|---|
| 1 | | | | | | | | | | | |
| 2 | | | | | | | | | | | |
| 3 | | | | | | | | | | | |
| 4 | | | | | | | | | | | |
| 5 | | | | | | THREAD DEPTH VALUES | | | | | |
| 6 | | | RADIUS | | | | | | | | |
| 7 | PITCH | | 0.016 | 0.018 | 0.02 | 0.022 | 0.024 | 0.026 | 0.028 | 0.03 | |
| 8 | | 0.002 | 3.128E-05 | 2.780E-05 | 2.502E-05 | 2.274E-05 | 2.084E-05 | 1.924E-05 | 1.786E-05 | 1.667E-05 | |
| 9 | | 0.003 | 7.047E-05 | 6.261E-05 | 5.633E-05 | 5.120E-05 | 4.692E-05 | 4.331E-05 | 4.021E-05 | 3.752E-05 | |
| 10 | | 0.004 | 1.255E-04 | 1.115E-04 | 1.003E-04 | 9.110E-05 | 8.348E-05 | 7.704E-05 | 7.152E-05 | 6.674E-05 | |
| 11 | | 0.005 | 1.965E-04 | 1.745E-04 | 1.569E-04 | 1.425E-04 | 1.306E-04 | 1.205E-04 | 1.118E-04 | 1.043E-04 | |
| 12 | | 0.006 | 2.838E-04 | 2.518E-04 | 2.263E-04 | 2.055E-04 | 1.882E-04 | 1.737E-04 | 1.612E-04 | 1.504E-04 | |
| 13 | | 0.007 | 3.875E-04 | 3.436E-04 | 3.086E-04 | 2.802E-04 | 2.566E-04 | 2.367E-04 | 2.196E-04 | 2.049E-04 | |
| 14 | | 0.008 | 5.081E-04 | 4.501E-04 | 4.041E-04 | 3.667E-04 | 3.357E-04 | 3.095E-04 | 2.872E-04 | 2.679E-04 | |
| 15 | | 0.009 | 6.458E-04 | 5.716E-04 | 5.128E-04 | 4.651E-04 | 4.258E-04 | 3.924E-04 | 3.640E-04 | 3.394E-04 | |
| 16 | | 0.010 | 8.013E-04 | 7.084E-04 | 6.351E-04 | 5.757E-04 | 5.266E-04 | 4.853E-04 | 4.500E-04 | 4.196E-04 | |
| 17 | | 0.011 | 9.750E-04 | 8.609E-04 | 7.711E-04 | 6.986E-04 | 6.387E-04 | 5.884E-04 | 5.455E-04 | 5.085E-04 | |
| 18 | | 0.012 | 1.168E-03 | 1.029E-03 | 9.212E-04 | 8.340E-04 | 7.621E-04 | 7.018E-04 | 6.504E-04 | 6.061E-04 | |
| 19 | | 0.013 | 1.380E-03 | 1.215E-03 | 1.086E-03 | 9.822E-04 | 8.970E-04 | 8.256E-04 | 7.649E-04 | 7.126E-04 | |
| 20 | | 0.014 | 1.613E-03 | 1.417E-03 | 1.265E-03 | 1.143E-03 | 1.044E-03 | 9.600E-04 | 8.891E-04 | 8.281E-04 | |
| 21 | | 0.015 | 1.867E-03 | 1.637E-03 | 1.460E-03 | 1.318E-03 | 1.202E-03 | 1.105E-03 | 1.023E-03 | 9.526E-04 | |
| 22 | | 0.016 | 2.144E-04 | 1.875E-03 | 1.670E-03 | 1.506E-03 | 1.373E-03 | 1.261E-03 | 1.167E-03 | 1.086E-03 | |
| 23 | | | | | | | | | | | |

$P_1 \neq P_2 \neq P_3 \cdots$

FIG.8A $d_1 \neq d_2 \neq \cdots$

FIG.8B

PROSTHESIS INCLUDING A MECHANISM FOR ATTACHING A FIRST COMPONENT TO A SECOND COMPONENT

FIELD OF THE INVENTION

In one embodiment of the present invention a prosthesis including a mechanism for attaching a first component to a second component is provided.

In one example (which example is intended to be illustrative and not restrictive), the first component may be a femoral head component and the second component may be a femoral stem component.

In another example (which example is intended to be illustrative and not restrictive), the femoral head component may comprise a ceramic material and the femoral stem component may comprise a metallic material (e.g., any desired orthopedic alloy, such as Cobalt Chromium).

For the purposes of describing and claiming the present invention, the term "interference fit" is intended to refer to physical contact between two or more components.

Further, for the purposes of describing and claiming the present invention, the term "ridge face" is intended to refer to a surface forming a side portion of a ridge.

Figure 3:
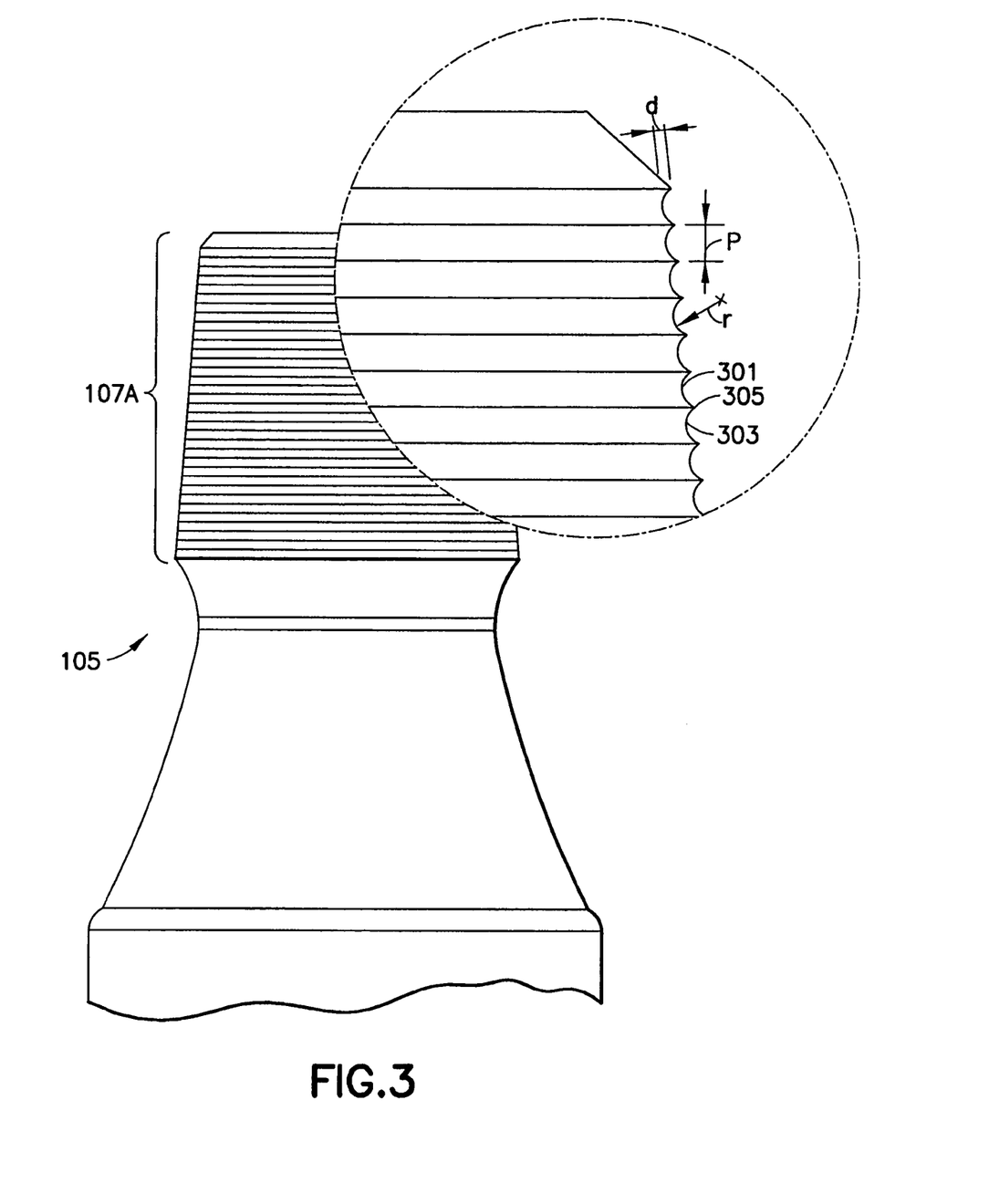
FIG. 3 shows a femoral stem of one example of the present invention in detail.
Figure 6:
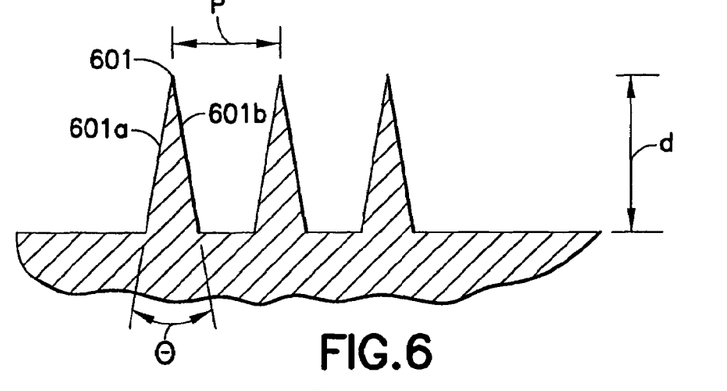
FIGS. 6 and 7 show ridge face profiles according to other examples of the present invention.
Figure 7:
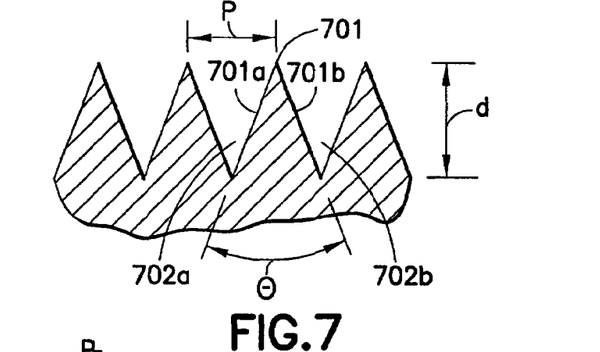

Further still, for the purposes of describing and claiming the present invention, the term "ridge apex" is intended to refer to the tip of a ridge where the "ridge faces" meet one another. To give a number of examples of what is meant by "ridge apex" (which examples are intended to be illustrative and not restrictive), reference is made to FIG. 3 showing the apex of Ridge 305, FIG. 6 showing the apex of Ridge 601 and FIG. 7 showing the apex of Ridge 701.

BACKGROUND OF THE INVENTION

Various systems for connecting components of a prosthesis together have been proposed.

See, for example, Richter, H. G., Willmann, G., Wimmer, M., and Osthues, F. G., "Influence of the Ball/Stem-Interface on the Load Bearing Capability of Modular Total Hip Endoprosthesis," Modularity of Orthopedic Implants, ASTM STP 1301, Donald E. Marlowe, Jack E. Parr, and Michael B. Mayor, Eds., American Society for Testing and materials, 1997 (hereinafter "Richter et al.").

More particularly, Richter et al. discusses a study in which "the surface structure of metal tapers is varied systematically in order to evaluate the influence of groove depth and pitch on the resistance to static load."

Additional examples of systems for connecting components of a prosthesis together include the systems described in the following U.S. patents:

U.S. Pat. No. 4,225,981 issued Oct. 7, 1980 to Zeibig relates to an endoprosthesis with a metal-ceramic union. More particularly, this patent relates to a bone joint endoprosthesis in which the spigot of the metal shank is externally threaded to mate with a thread inside the ceramic head of the prosthesis; the thread on the spigot has greater depth in the radial direction, with flat sides, and the depth of the thread in the head is more shallow.

U.S. Pat. No. 5,584,629 issued Dec. 17, 1996 to Bailey et al. relates to a connector for medical implant. More particularly, this patent relates to a connection for components in a medical implant assembly which utilizes a tapered mating surface on each component with cylindrical splines and flutes formed on each mating surface such that the surfaces are complementary to the extent that the splines of one surface are received in the flutes of the adjacent surface. The patent indicates that each surface is continuous with no discontinuity which would act as a stress raiser or enhance concentration of stress in one locale. The complementary surfaces are urged into registry by a screw connection coaxially through the surfaces.

U.S. Pat. No. 5,865,850 issued Feb. 2, 1999 to Matthews relates to a coated load bearing surface for a prosthetic joint. More particularly, this patent relates to a prosthetic hip joint including a ceramic hip head having a bore which defines a surface, wherein the bore surface has a layer of malleable material disposed on at least a portion thereof. The surface of the bore includes surface imperfections in the form of peaks and valleys. The prosthetic hip joint can also include a femoral component having a trunnion with a tapered surface adapted for friction fit insertion into the bore of the hip head. The patent indicates that the layer of material, such as pure titanium, distributes a load on the joint reducing localized stress points produced by opposing asperity peaks in the load-bearing surfaces of the bore and trunnion.

Among those benefits and improvements that have been disclosed, other objects and advantages of this invention will become apparent from the following description taken in conjunction with the accompanying figures. The figures constitute a part of this specification and include illustrative embodiments of the present invention and illustrate various objects and features thereof.

DETAILED DESCRIPTION OF THE INVENTION

Detailed embodiments of the present invention are disclosed herein; however, it is to be understood that the disclosed embodiments are merely illustrative of the invention that may be embodied in various forms. In addition, each of the examples given in connection with the various embodiments of the invention are intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

Figure 1:
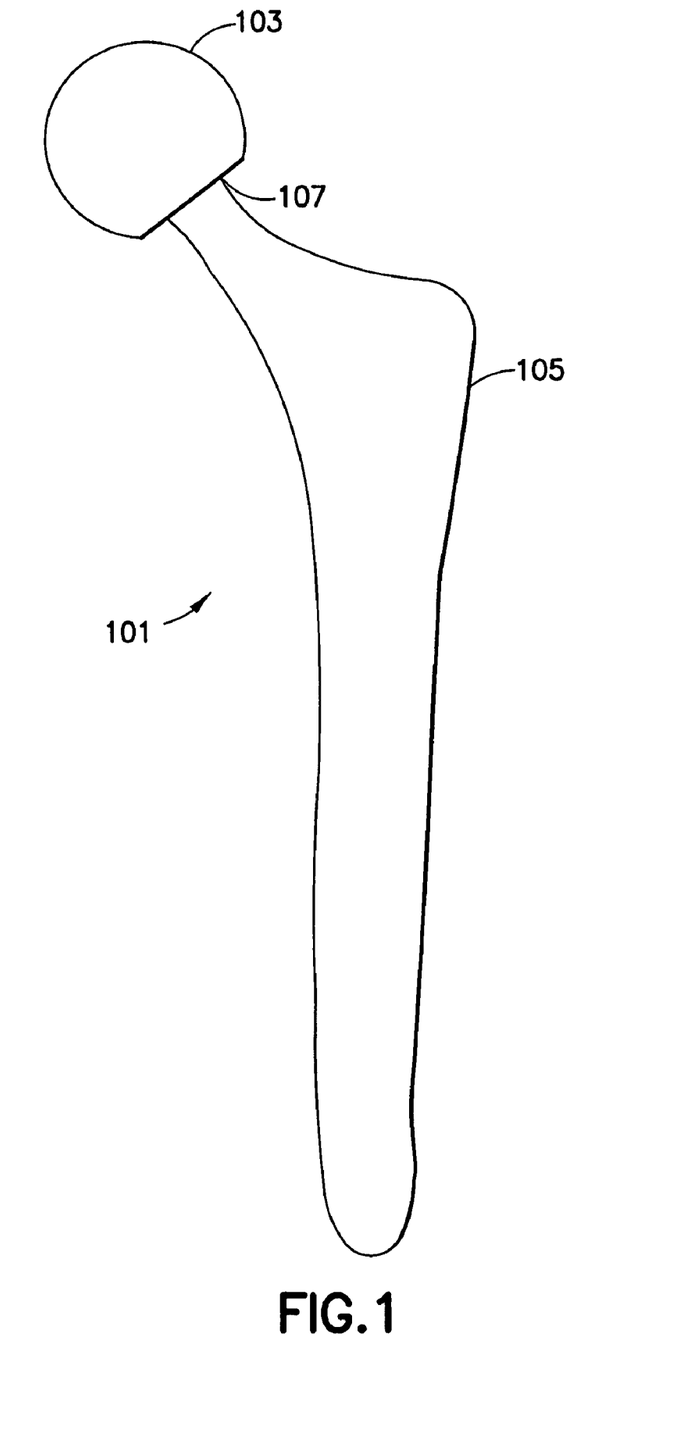
FIG. 1 shows a prosthetic device including a femoral head and a femoral stem attached according to an embodiment of the present invention.
Figure 2:
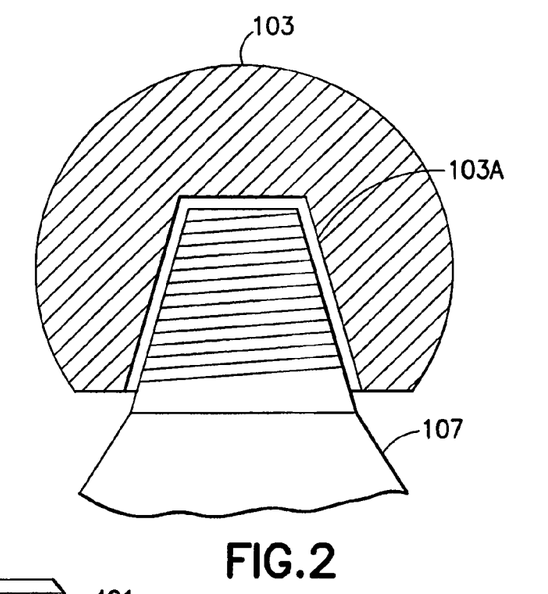
FIG. 2 shows a cross section of the femoral stem of FIG. 1 received by the femoral head of FIG. 1.

Referring now to FIGS. 1 and 2, one embodiment of the present invention is shown. As seen in these Figs., Prosthetic Device 101 may include a first component attached to a second component. More particularly, in one example (which example is intended to be illustrative and not restrictive), the first component may comprise Femoral Head 103 and the second component may comprise Femoral Stem 105. In another example Femoral Head 103 may comprise a ceramic material and Femoral Stem 105 may comprise a metallic material (e.g., Cobalt Chromium).

Further, Femoral Head 103 may include a female recess (defined by Recess Wall 103A) for receiving Male Extension 107 (e.g., "trunnion") associated with Femoral Stem 105 (see FIG. 2).

In addition, the female recess may taper from wider to narrower in a direction moving from an exterior surface of Femoral Head 103 towards an interior of Femoral Head 103 and at least part of an exterior surface of Male Extension 107 may taper from wider to narrower in a direction moving towards an end of Male Extension 107.

Moreover, the female recess may be configured to receive at least part of the exterior surface of Male Extension 107 such that, when the female recess receives Male Extension 107, Male Extension 107 and the female recess are mated together via an interference fit (i.e., an interference fit between at least part of the exterior surface of Male Extension 107 and at least part of Recess Wall 103A).

Referring now to FIG. 3, certain details of Femoral Stem 105 in connection with one example of the present invention (which example is intended to be illustrative and not restrictive) are shown. More particularly, it is seen that Femoral Stem 105 may include Male Extension 107A having disposed on at least a part of its exterior surface a plurality of grooves and a plurality of ridges. In this regard, details of these grooves and ridges are shown in the circled detail portion of FIG. 3 (of note, only Groove 301, Groove 303 and Ridge 305 are separately called out with numerical identifiers in this Fig.).

In any case, it is seen that Grooves 301 and 303 may be disposed adjacent one another such that Ridge 305 is formed between Grooves 301 and 303. Further, it is seen that Ridge 305 has a first ridge face formed by Groove 301 and that Ridge 305 has a second ridge face formed by Groove 303. Moreover, it is seen that the first ridge face and the second ridge face of Ridge 305 meet at a ridge apex.

Still referring to FIG. 3, it is seen that the measurement identified by the letter "d" may specify the depth of the grooves (for example, as measured from a ridge apex to a bottom of a groove), that the measurement identified by the letter "p" may specify the pitch of the groove/ridge topography (for example, as measured from one ridge apex to the next) and that the measurement identified by the letter "r" may specify the radius of the grooves (for example, as measured to the bottom of a groove).

Figure 4:
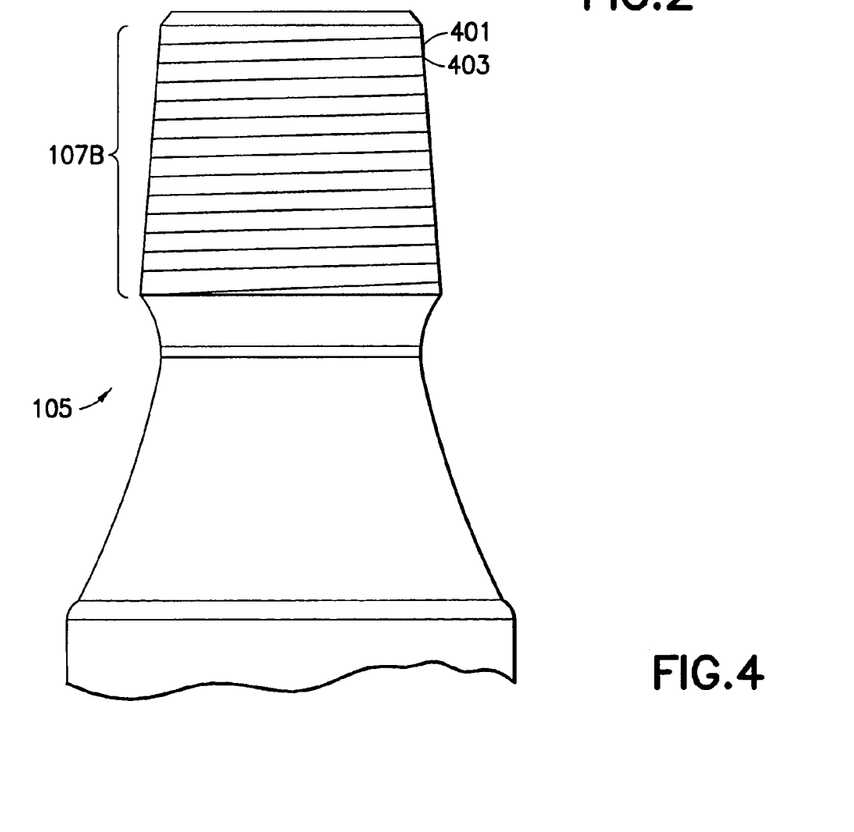
FIG. 4 shows a femoral stem of another example of the present invention in detail.

Of note, the ridges and grooves of this FIG. 3 may be essentially parallel to one another and may form discrete concentric elements along Male Extension 107A. In contrast, reference is now made to the example of FIG. 4 (which example is intended to be illustrative and not restrictive). More particularly, this FIG. 4 depicts a single helical thread on Male Extension 107B. That is, Groove 401 and Ridge 403 wrap around and around Male Extension 107B in an essentially continuous manner. Of note, the surface profile of Male Extension 107B may otherwise be similar to that of Male Extension 107A of FIG. 3 (e.g., with regard to the "d", "p" and "r" dimensions and with regard to the fact that Ridge 403 has a ridge apex blending essentially directly into the groove).

Referring now to the attachment of Femoral Stem 105 to Femoral Head 103, it is noted that one or more ridges may be configured to deform against Recess Wall 103A of the female recess. More particularly, in one example (which example is intended to be illustrative and not restrictive), one or more ridge apexes may be configured to deform against Recess Wall 103A of the female recess. In this regard, it is noted that the substantial amount of deformation provided by the ridge apexes may provide for a strong attachment with advantageous stress/strain characteristics.

Figure 5A:
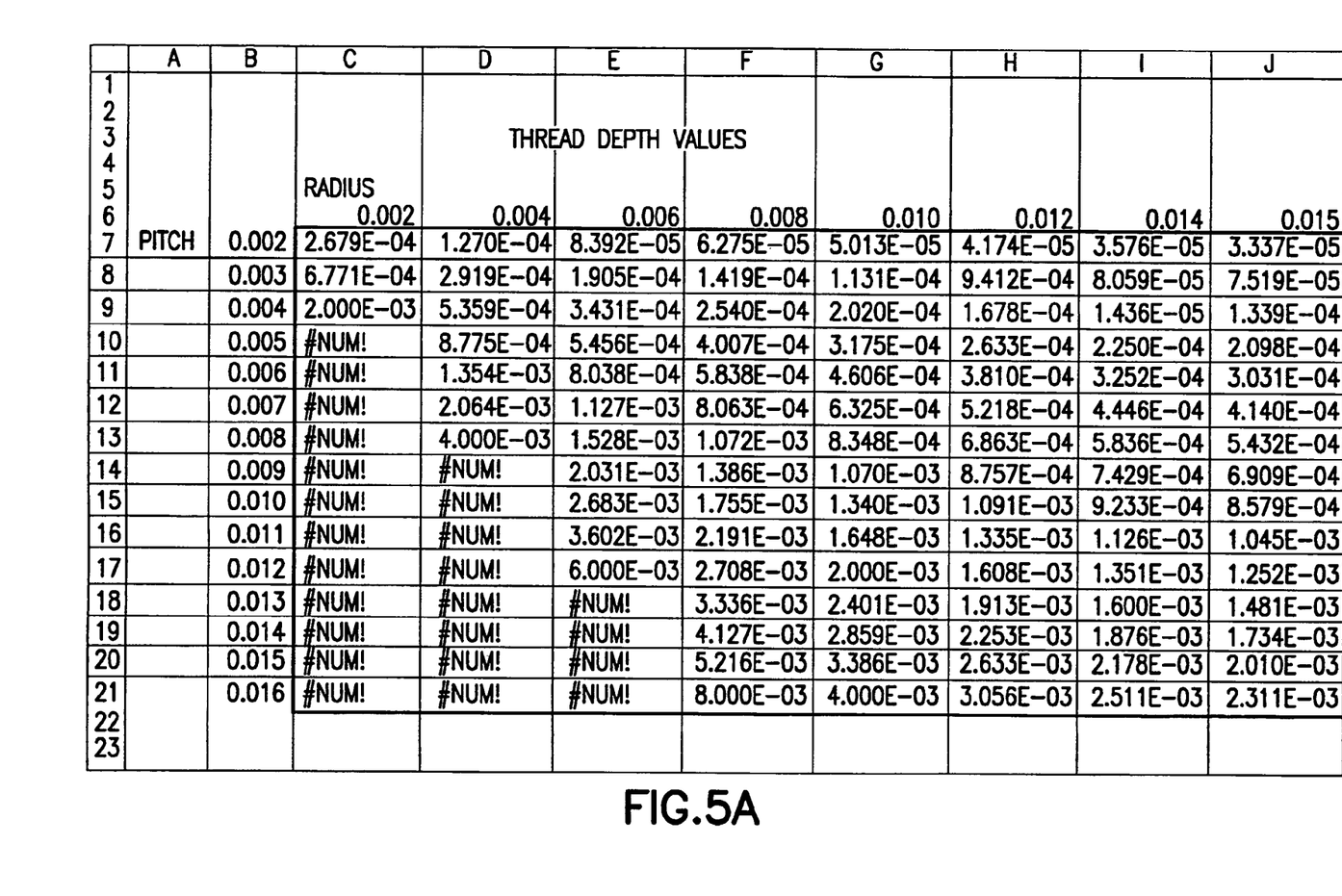
FIGS. 5A and 5B show a table with example surface geometry characterizations relating to the present invention.
Figure 5B:
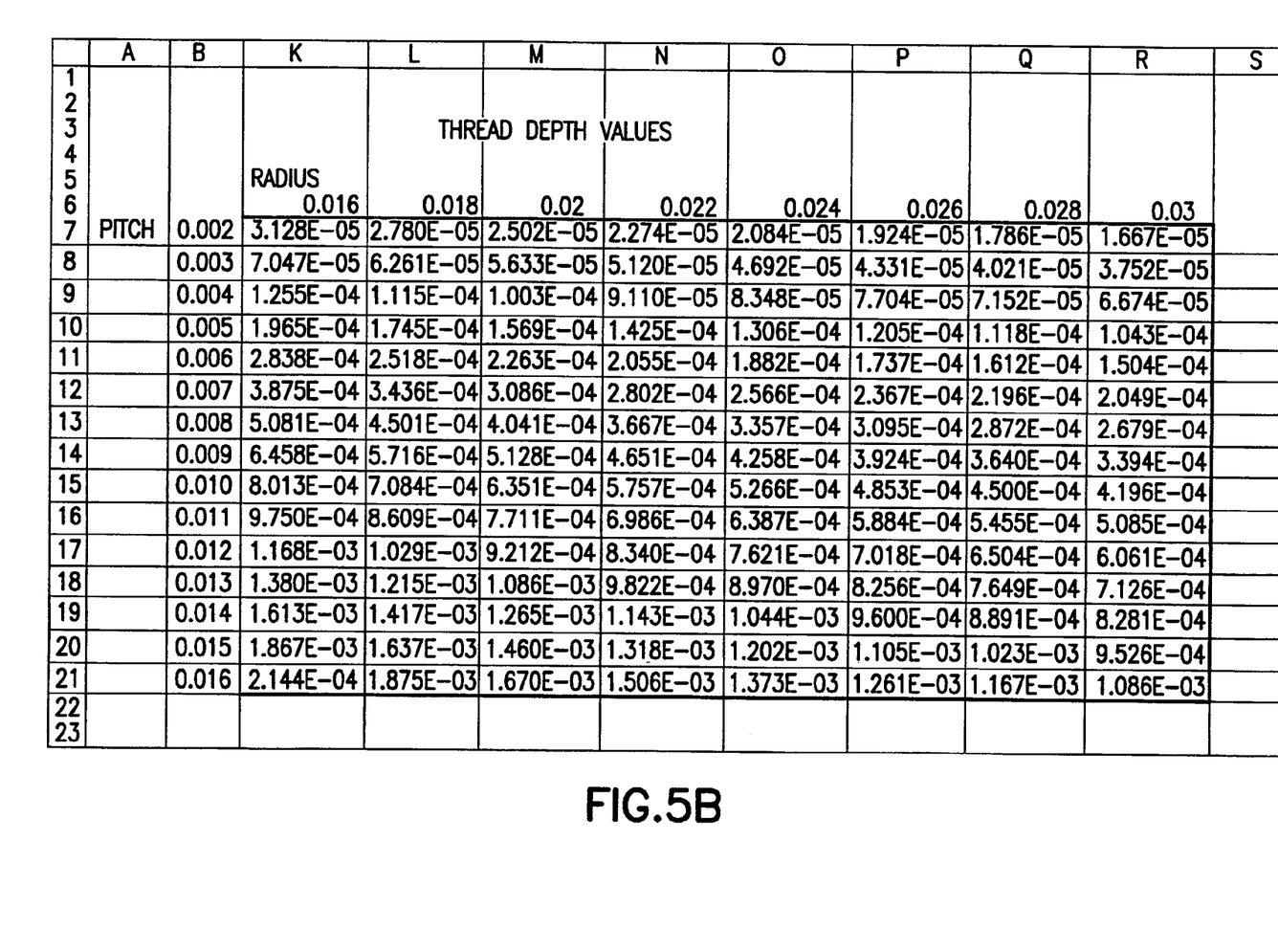

Reference will now be made to FIGS. 5A and 5B showing, respectively, the left-hand portion and the right-hand portion of a table depicting example radius, pitch and depth values which may be applied to the embodiments of FIGS. 3 and 4 (of course, the examples of this table are intended to be illustrative and not restrictive). Of note, the pitch values of this table (i.e., the variables along column "B") refer to the pitch identification "p" in FIGS. 3 and 4, the radius values of this table (i.e., the variables along row "6") refer to the radius identification "r" in FIGS. 3 and 4 and the depth values of this table (i.e., the result of carrying out the computations using the various pitch and radius values) refer to the depth identification "d" in FIGS. 3 and 4 (the values shown in this table are in inches). Of further note, the depth values in this table are the result of the following computation:

$$d = r - \sqrt{r^2 - (p/2)^2}$$

Still referring to FIGS. 5A and 5B, it is noted that certain combinations of radius and pitch may be physically impossible to realize (see, e.g., column "C", rows 10-21; column "D", rows 14-21; and column "E", rows 18-21) and certain combinations of radius and pitch may be very difficult to manufacture (see, e.g., column "C", row 9; column "D", row 13; column "E", row 17; and column "F", row 21).

Moreover, it is noted that various combinations of radius and pitch may result in geometries having various burst strengths when applied, for example, to a metallic femoral stem component which is inserted into a ceramic femoral head component.

More particularly, tests have revealed, for example, that a combination of r=0.008 and p=0.008 (resulting in d=1.072E-3) has a burst strength of 47 kN when a Cobalt Chromium femoral stem component is inserted into a ceramic femoral head component; that a combination of r=0.015 and p=0.010 (resulting in d=8.579E-4) has a burst strength of 43 kN when a Cobalt Chromium femoral stem component is inserted into a ceramic femoral head component; and that a combination of r=0.03 and p=0.016 (resulting in d=1.086E-3) has a burst strength of 38 kN when a Cobalt Chromium femoral stem component is inserted into a ceramic femoral head component.

In addition, it is noted that in general burst strength may be increased (up to a point) by increasing depth/decreasing pitch. In this regard, it is believed, for example, that the combinations of r=0.002 and p=0.002 to 0.003; r=0.004 and p=0.002 to 0.007; r=0.006 and p=0.002 to 0.011; r=0.008 and p=0.002 to 0.015; r=0.010 and p=0.002 to 0.016; r=0.012 and p=0.002 to 0.016; r=0.014 and p=0.002 to 0.016; and r=0.015 and p=0.012 to 0.016 would likely have a burst strength greater than 47 kN.

Finally, it is noted that specific r, p and/or d values may be chosen for any particular implementation in order to meet any desired criteria (e.g., minimum burst strength). For example (which example is intended to be illustrative and not restrictive), r, p and/or d values may be chosen to meet a current FDA requirement of >46 kN with Cobalt Chromium alloys (which are relatively rigid and hard compared to Titanium Aluminum Vanadium, for example).

Referring now to FIGS. 6 and 7, two additional ridge face profiles (in addition to the profiles already shown in the proceeding Figs.) are shown.

More particularly, FIG. 6 shows a substantially flat ridge face profile in which Ridge 601 comprises First Ridge Face 601a and Second Ridge Face 601b meeting at the apex of Ridge 601. Of note, First Ridge Face 601a and Second Ridge Face 601b may have any desired angle "θ", any desired spacing "p" and any desired depth "d". Of further note, Ridge 601 may "rise up" from the underlying surface rather than be formed by grooves "cut into" the surface. Of still further note, only Groove 601, First Ridge Face 601a and Second Ridge Face 601b are separately called out with numerical identifiers in this Fig. (the other ridges/ridge faces are not separately called out with numerical identifiers).

Further, FIG. 7 shows a substantially flat ridge face profile in which Ridge 701 comprises First Ridge Face 701a and Second Ridge Face 701b meeting at the apex of Ridge 701. Of note, First Ridge Face 701a and Second Ridge Face 701b may have any desired angle "θ", any desired spacing "p" and any desired depth "d". Of further note, Ridge 701 may be formed by Grooves 702a and 702b in a manner similar to that shown in FIGS. 3 and 4, for example (rather than "rising up" from the underlying surface as shown in FIG. 6). Of still further note, only Ridge 701, First Ridge Face 701a, Second Ridge Face 701b and Grooves 702a, 702b are separately called out with numerical identifiers in this Fig. (the other grooves/ridges/ridge faces are not separately called out with numerical identifiers).

Figure 8A:
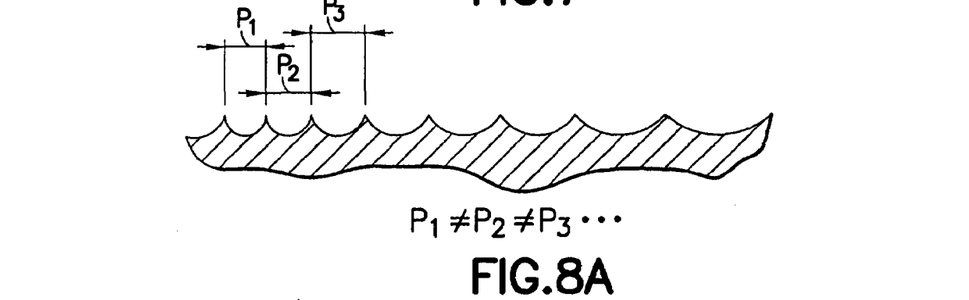
FIGS. 8A and 8B show varied pitch and depth according to other examples of the present invention.

Referring now to FIG. 8A, it is seen that the pitch "p" may vary (e.g., the pitch "p" may vary over the taper length of the male extension). This varied pitch may provide differing magnitudes of contact stresses to different parts of the male extension and/or the female recess/femoral head.

Figure 8B:
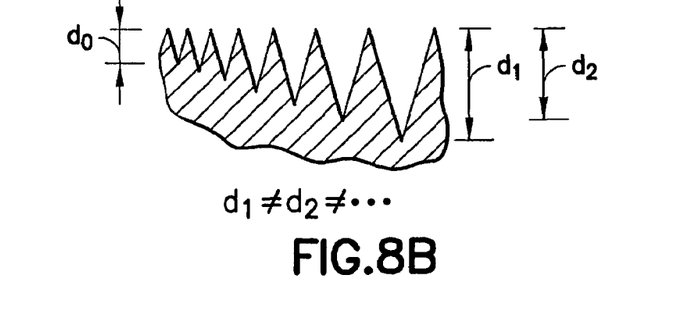

Referring now to FIG. 8B, it is seen that the depth "d" may vary (e.g., the depth "d" may vary over the taper length of the male extension). This varied depth may likewise provide differing magnitudes of contact stresses to different parts of the male extension and/or the female recess/femoral head. Of course, either or both of the pitch and/or depth may be varied as desired.

While a number of embodiments of the present invention have been described, it is understood that these embodiments are illustrative only, and not restrictive, and that many modifications may become apparent to those of ordinary skill in the art. For example, the present invention may be applied to a prosthesis for use anywhere in or on the body. Further, any element described herein may be provided in any desired size (e.g., any element described herein may be provided in any desired custom size or any element described herein may be provided in any desired size selected from a "family" of sizes, such as small, medium, large). Further still, one or more of the ridge faces may be flat and/or curved convexly and/or curved concavely. Further still, the male extension may take any desired shape (rather than being in the form of an essentially circular truncated cone as shown in the figures). Further still, the female recess may take any desired shape (rather than being in the form of an essentially circular truncated cone as shown in the figures). Further still, the recess wall may have any desired topography (rather than being flat as shown in the figures). Further still, the taper angle of the femoral head and/or femoral stem may be any desired taper angle (e.g., a nominal 12/14 taper angle). Further still, any component of the prosthesis adapted to attach to and/or in bone (e.g., a femoral stem) may include any desired surface treatment (e.g., a thread for screwing into bone, surface irregularities for aiding in fixation (e.g., protrusions, indentations), slots, sandblasting, knurling, etc). Further still, the present invention may provide a mechanism via which the stresses developed in the prosthesis (e.g., in the ceramic head) may be designed for any desired value (e.g., may be designed to meet loading levels mandated by the FDA). Further still, the present invention may provide a mechanism to accommodate inaccuracies in the interface between components of the prosthesis (for example, between a femoral stem component which is inserted into a femoral head component). Further still, one or more of the components of the prosthesis may include any of the following materials: (a) any biocompatible material (which biocompatible material may be treated to permit bone ingrowth or prohibit bone ingrowth—depending upon the desire of the surgeon); (b) a plastic; (c) a fiber; (d) a polymer; (e) a pure metal; (f) a metal alloy (e.g., Cobalt Chromium, Titanium Aluminum Vanadium); (g) a ceramic; (h) any combination thereof. Further still, while variable pitch and depth parameters (e.g., over at least a part of the length of the male extension) have been discussed, any groove and/or ridge parameters may be varied as desired. Further still, any steps described herein may be carried out in any desired order.

What is claimed is:

1. A prosthetic device, comprising:
   a first component including a female recess; and
   a second component including a male extension, which male extension has disposed on at least a part of an exterior surface a plurality of grooves and a plurality of ridges;
   wherein the female recess is defined by a recess wall and the female recess tapers from wider to narrower in a direction moving from an exterior surface of the first component towards an interior of the first component;
   wherein at least part of the exterior surface of the male extension which has disposed thereon the plurality of grooves and ridges tapers from wider to narrower in a direction moving towards a first end of the male extension;
   wherein the plurality of grooves are disposed adjacent one another such that the ridges are formed between the grooves;
   wherein each ridge has a first ridge face formed by a respective groove and a second ridge face formed by a respective groove;
   wherein the first ridge face and second ridge face of each ridge meet at a ridge apex; and
   wherein the female recess is configured to receive at least part of the exterior surface of the male extension which has disposed thereon the plurality of grooves and ridges; and
   wherein the male extension and the female recess are sized such that, when the female recess receives the male extension, the male extension and the female recess are directly mated together via an interference fit.

2. The prosthetic device of claim 1, wherein the ridge apex of each ridge disposed upon the part of the exterior surface of the male extension received by the female recess is configured to deform against the recess wall of the female recess.

3. The prosthetic device of claim 1, wherein the first component is a femoral head.

4. The prosthetic device of claim 3, wherein the femoral head comprises a ceramic material.

5. The prosthetic device of claim 1, wherein the recess wall is substantially flat.

6. The prosthetic device of claim 1, wherein at least a portion of the female recess is in the form of a truncated cone.

7. The prosthetic device of claim 1, wherein the second component is a femoral stem.

8. The prosthetic device of claim 7, wherein the femoral stem comprises a metallic material.

9. The prosthetic device of claim 8, wherein the metallic material is Cobalt Chromium.

10. The prosthetic device of claim 1, wherein at least a portion of the male extension is in the form of a truncated cone.

11. The prosthetic device of claim 1, wherein the ridges are substantially parallel to one another.

12. The prosthetic device of claim 1, wherein each of the ridge faces has a profile that is concave.

13. The prosthetic device of claim 1, wherein a spacing between one pair of adjacent ridge apexes is different from a spacing between another pair of adjacent ridge apexes.

14. The prosthetic device of claim 1, wherein a depth of at least a first groove is different from a depth of at least a second groove.

15. The prosthetic device of claim 1, wherein each of the ridge faces has a curved profile, wherein "r" represents a radius of the curved profile, wherein "p" represents a spacing between a pair of adjacent ridge apexes and wherein the values of "r" and "p" are selected from the group consisting of:
   a) "r" is in the range of about 0.002 inch to about 0.014 inch and "p" is in the range of about 0.002 inch to about 0.003 inch,
   b) "r" is in the range of about 0.004 inch to about 0.014 inch and "p" is in the range of about 0.004 inch to about 0.007 inch,
   c) "r" is in the range of about 0.006 inch to about 0.014 inch and "p" is in the range of about 0.008 inch to about 0.011 inch,
   d) "r" is in the range of about 0.008 inch to about 0.015 inch and "p" is in the range of about 0.012 inch to about 0.015 inch, and
   e) "r" is in the range of about 0.010 inch to about 0.015 inch and "p" is about 0.016 inch.

16. A prosthetic device, comprising:
a femoral head including a female recess; and
a femoral stem including a male extension, which male extension has disposed on at least a part of an exterior surface a plurality of grooves and a plurality of ridges;
wherein the female recess is defined by a recess wall and the female recess tapers from wider to narrower in a direction moving from an exterior surface of the femoral head towards an interior of the femoral head;
wherein at least part of the exterior surface of the male extension which has disposed thereon the plurality of grooves and ridges tapers from wider to narrower in a direction moving towards a first end of the male extension;
wherein the plurality of grooves are disposed adjacent one another such that the ridges are formed between the grooves;
wherein each ridge has a first ridge face formed by a respective groove and a second ridge face formed by a respective groove;
wherein the first ridge face and second ridge face of each ridge meet at a ridge apex;
wherein the recess wall is substantially flat;
wherein at least a portion of the female recess is in the form of a truncated cone;
wherein at least a portion of the male extension is in the form of a truncated cone;
wherein the femoral head comprises a ceramic material;
wherein the femoral stem comprises a metallic material;
wherein the female recess is configured to receive at least part of the exterior surface of the male extension which has disposed thereon the plurality of grooves and ridges;
wherein the male extension and the female recess are sized such that, when the female recess receives the male extension, the male extension and the female recess are directly mated together via an interference fit; and
wherein the ridge apex of each ridge disposed upon the part of the exterior surface of the male extension received by the female recess is configured to deform against the recess wall of the female recess.

17. The prosthetic device of claim 16, wherein the metallic material is Cobalt Chromium.

18. The prosthetic device of claim 16, wherein the ridges are substantially parallel to one another.

19. The prosthetic device of claim 16, wherein each of the ridge faces has a profile that is concave.

20. The prosthetic device of claim 16, wherein a spacing between one pair of adjacent ridge apexes is different from a spacing between another pair of adjacent ridge apexes.

21. The prosthetic device of claim 16, wherein a depth of at least a first groove is different from a depth of at least a second groove.

22. The prosthetic device of claim 16, wherein each of the ridge faces has a curved profile, wherein "r" represents a radius of the curved profile, wherein "p" represents a spacing between a pair of adjacent ridge apexes and wherein the values of "r" and "p" are selected from the group consisting of:
   a) "r" is in the range of about 0.002 inch to about 0.014 inch and "p" is in the range of about 0.002 inch to about 0.003 inch,
   b) "r" is in the range of about 0.004 inch to about 0.014 inch and "p" is in the range of about 0.004 inch to about 0.007 inch,
   c) "r" is in the range of about 0.006 inch to about 0.014 inch and "p" is in the range of about 0.008 inch to about 0.011 inch,
   d) "r" is in the range of about 0.008 inch to about 0.015 inch and "p" is in the range of about 0.012 inch to about 0.015 inch, and
   e) "r" is in the range of about 0.010 inch to about 0.015 inch and "p" is about 0.016 inch.

* * * * *